United States Patent
Yost et al.

(10) Patent No.: US 6,746,410 B2
(45) Date of Patent: Jun. 8, 2004

(54) METHOD AND APPARATUS FOR DETERMINING CHANGES IN INTRACRANIAL PRESSURE UTILIZING MEASUREMENT OF THE CIRCUMFERENTIAL EXPANSION OR CONTRACTION OF A PATIENT'S SKULL

(75) Inventors: William T. Yost, Newport News, VA (US); John H. Cantrell, Jr., Williamsburg, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 226 days.

(21) Appl. No.: 10/121,932

(22) Filed: Apr. 4, 2002

(65) Prior Publication Data

US 2003/0191409 A1 Oct. 9, 2003

(51) Int. Cl.$^7$ ................................. A61B 5/02
(52) U.S. Cl. ........................................ 600/561
(58) Field of Search ....................... 600/561, 438

(56) References Cited

U.S. PATENT DOCUMENTS

| | | | |
|---|---|---|---|
| 4,971,061 A | 11/1990 | Kageyama et al. | |
| 5,074,310 A | * 12/1991 | Mick | 600/587 |
| 5,214,955 A | 6/1993 | Yost et al. | |
| 5,251,627 A | * 10/1993 | Morris | 600/398 |
| 5,388,583 A | 2/1995 | Ragauskas et al. | |
| 5,617,873 A | 4/1997 | Yost et al. | |
| 5,951,476 A | 9/1999 | Beach | |
| 6,117,089 A | 9/2000 | Sinha | |
| 6,210,346 B1 | 4/2001 | Hall et al. | |
| 6,231,509 B1 | 5/2001 | Johnson et al. | |
| 6,264,611 B1 | 7/2001 | Ishikawa et al. | |
| 6,413,227 B1 | 7/2002 | Yost et al. | |
| 6,475,147 B1 | 11/2002 | Yost et al. | |
| 2003/0171693 A1 | 9/2003 | Yost et al. | |
| 2003/0191410 A1 | 10/2003 | Yost et al. | |
| 2003/0191411 A1 | 10/2003 | Yost et al. | |

FOREIGN PATENT DOCUMENTS

WO  WO 00/68647  11/2000

OTHER PUBLICATIONS

Toshiaki Ueno et al., "Effects of Whole Body Tilting on Intracranial Pressure Dynamics,".
Toshiaki Ueno et al., "Noninvasive Measurement of Pulsatile Intracranial Pressure Using Ultrasound," Acta Neurochir, p. 66–69, (Dec. 23, 1998).

* cited by examiner

Primary Examiner—Eric F. Winakur
(74) Attorney, Agent, or Firm—Helen M. Galus

(57) ABSTRACT

A method and apparatus for measuring changes in intracranial pressure (ICP) utilizing the variation of the surface wave propagation parameters of the patient's skull to determine the change in ICP. In one embodiment, the method comprises the steps of transmitting an ultrasonic bulk compressional wave onto the surface of the skull at a predetermined angle with respect to the skull so as to produce a surface wave, receiving the surface wave at an angle with respect to the skull which is substantially the same as the predetermined angle and at a location that is a predetermined distance from where the ultrasonic bulk compressional wave was transmitted upon the skull, determining the retardation or advancement in phase of the received surface wave with respect to a reference phase, and processing the determined retardation or advancement in phase to determine circumferential expansion or contraction of the skull and utilizing the determined circumferential change to determine the change in intracranial pressure.

31 Claims, 2 Drawing Sheets

METHOD AND APPARATUS FOR DETERMINING CHANGES IN INTRACRANIAL PRESSURE UTILIZING MEASUREMENT OF THE CIRCUMFERENTIAL EXPANSION OR CONTRACTION OF A PATIENT'S SKULL

ORIGIN OF THE INVENTION

The invention described herein was made by employees of the United States Government and may be used by or for the Government for governmental purposes without the payment of any royalties thereon or therefor.

BACKGROUND OF THE INVENTION

1. Technical Field of the Invention

The present invention relates broadly to the field of apparatuses and methods for determining changes in intracranial pressure ("ICP") by measuring the effects of these changes on a patient's skull.

2. Related Art and Problem to be Solved

Monitoring circumferential expansion of the patient's skull due to changes in ICP is of significant diagnostic and post-operative importance for patients with cranial injuries, pathologies, or other conditions that may affect the pressure of the subarachnoidal fluid around the brain, and for patients who have undergone brain surgery.

Known art methods and techniques for measuring changes in circumferential expansion of the patient's skull due to changes in ICP frequently involve launching an ultrasonic bulk compressional wave through the cranium. This technique can require that the position of the transducer be essentially absolutely stable, relative to the patient's skull, during data acquisition. However, one significant problem with the aforesaid known art method is the difficulty in keeping the transducers immobile relative to the patient's skull for long periods of time. Thus, inaccurate or inconclusive data may result due to transducer movement.

It is an object of the present invention to provide a non-invasive method and apparatus for determining changes in ICP in a manner which does not require the transmission of a wave through the cranium.

It is another object of the present invention to provide a new method and apparatus for determining changes in ICP by measuring changes in circumferential expansion or contraction of the patient's skull.

It is another object of the present invention to provide a method and apparatus for determining changes in ICP, that provides substantially absolute stability of the transducer, relative to the patient's skull, during data acquisition.

Other objects and advantages of the present invention will in part be obvious and will in part be apparent from the specification.

SUMMARY OF THE INVENTION

The apparatus and method of the present invention use the variation of the surface wave propagation parameters of the patient's skull to determine the change in ICP.

In accordance with one embodiment of the invention, the apparatus comprises a measuring device, transmit and receive transducers, and transmit and receive angle blocks wherein the transmit and receive transducers are mounted to the transmit and receive angle blocks, respectively. The transmit and receive angle blocks each have surfaces that are configured to contact the skull. The apparatus further includes a mounting strut to which the transmit and receive angle blocks are movably attached. The mounting strut is adjustable in overall length so as to accommodate skulls of varying sizes, and to provide stability to the transducers.

In one embodiment, the measuring device is configured as a constant frequency pulsed phase-locked loop ("CFPPLL") measuring device.

The mounting strut can be adjusted on the skull so that the surface wave can be launched over a relatively small propagation path, for example, so the surface wave can travel across the forehead, or across a section of the skull containing a suture, or any other appropriate segment of the skull. Further, it is within the scope of the present invention that multiple pairs of tranducers (and angle blocks) could be used to launch (and receive) multiple surface waves over more than one propagation path. In this way, a differential comparison could then be made between the measured changes in ICP relative to each path. However, in at least one embodiment, each path may need to be calibrated separately and/or have different measurement interpretive algorithms associated therewith (see below).

In at least one embodiment, the measuring device generates an electrical tone burst which is inputted into the transmit transducer. The transmit transducer converts the electrical tone burst into a sound wave, such as an ultrasound bulk compressional wave that passes through the transmit angle block. The bulk compressional wave is then emitted into the skin and subcutaneous tissue that surrounds the skull at a predetermined angle so as to create a surface wave upon the skull. The surface wave travels over a propagation path and through the tissue that contacts the receive angle block. The receive angle block receives the surface wave at an angle that is generally the same as the aforementioned predetermined angle. The receive angle block converts the surface wave into an ultrasonic bulk compressional wave which is then received by the receive transducer. The receive transducer converts the ultrasonic bulk compressional wave back into an electrical tone burst which is inputted into the measurement device.

The transmit and receive transducers could take various forms, for example: piezoelectric, magnetostrictive, or electrodynamic. Moreover, bone is mildly piezoelectric, therefore, in another possible embodiment, one could induce and detect a surface wave with electromagnetic transducers and essentially avoid potential problems with skin tissue perfusion variability.

In at least one embodiment, the measurement device compares the phase of the electrical tone burst outputted by the receive transducer to a reference phase in order to determine if there is a difference in phase. As the skull responds to the changes in intracranial pressure, the velocity of the surface wave changes thereby resulting in retardation or advancement of the phase of the surface wave received by the receive angle block. Thus, the measurement device determines whether there has been any phase retardation or advancement. The measurement device outputs a data signal that represents the measured phase change.

It is within the scope of the present invention that a variety of surface waves could be propagated on the skull. Examples of these surface waves may include, Rayleigh, Rayleigh-type, Generalized Rayleigh, Leaky (or psuedo-), Bleustein-Gulynev, Shear Horizontal, Lamb, Generalized Lamb, Love, and Stoneley waves. Additionally, as used herein, the term "sound wave" is used to refer to the propogation of a disturbance, resultant from the disturbing of substantially any medium.

The apparatus of the present invention can further include a processing device that receives the data signal outputted by the measurement device and performs measurement interpretative algorithms on the data signal in order to determine the degree of circumferential expansion (or contraction) of the skull due to changes in ICP. This degree of circumferential expansion (or contraction) can be determined as a change to the total circumference of the skull or as a change to a circumferential arc portion of the skull.

In at least one embodiment, the measurement interpretive algorithms can implement a biological time constant (for example, representing pulse rate, respiration, etc.) during interpretation of the data contained in the data signal outputted by the measuring device. In one embodiment, the processing device can be realized by a computer program that is configured to provide functions as filtering, integrating, averaging, etc. In another embodiment, the processing device is configured with electronic components that can provide the aforesaid functions.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

In describing the embodiments of the present invention, reference will be made herein to FIGS. 1 and 2 of the drawings in which like numerals refer to like features of the invention.

Figure 1:
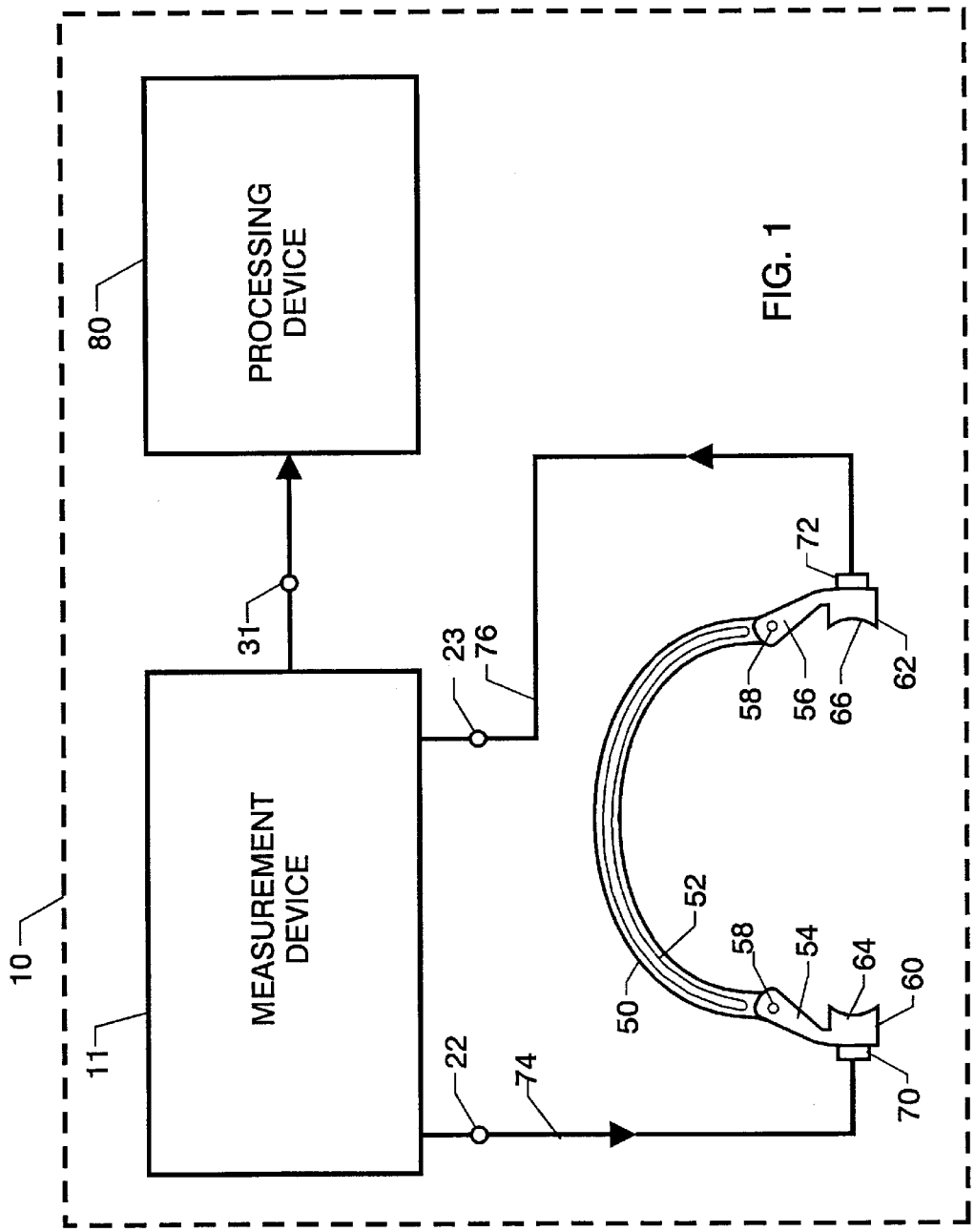
FIG. 1 is a block diagram of an apparatus of the present invention.

Referring to FIG. 1, there is shown apparatus 10 of the present invention. Apparatus 10 comprises measurement device 11. In one embodiment, the measurement device can be configured as a CFPPLL described in commonly owned U.S. Pat. No. 5,214,955, the disclosure of which is herein incorporated by reference as if set forth in its entirety. The CFPPLL is shown in FIG. 2 and is briefly described in the ensuing description in order to facilitate understanding of the present invention. The CFPPLL is configured to operate in the "pitch-catch" mode which is described in the aforementioned U.S. Pat. No. 5,214,955. In another embodiment, the measurement device 11 might comprise a variable frequency pulsed phase-locked loop ("VFPPLL"), for example as described in the article by Yost, et al., *Fundamental Aspects of Pulse Phase-locked Loop Technology-based Methods for Measurement of Ultrasonic Velocity*, J. Acoust. Soc. Am. 91, 1456–1468 (1992), which article is incorporated herein by reference as if set forth in its entirety.

Figure 2:
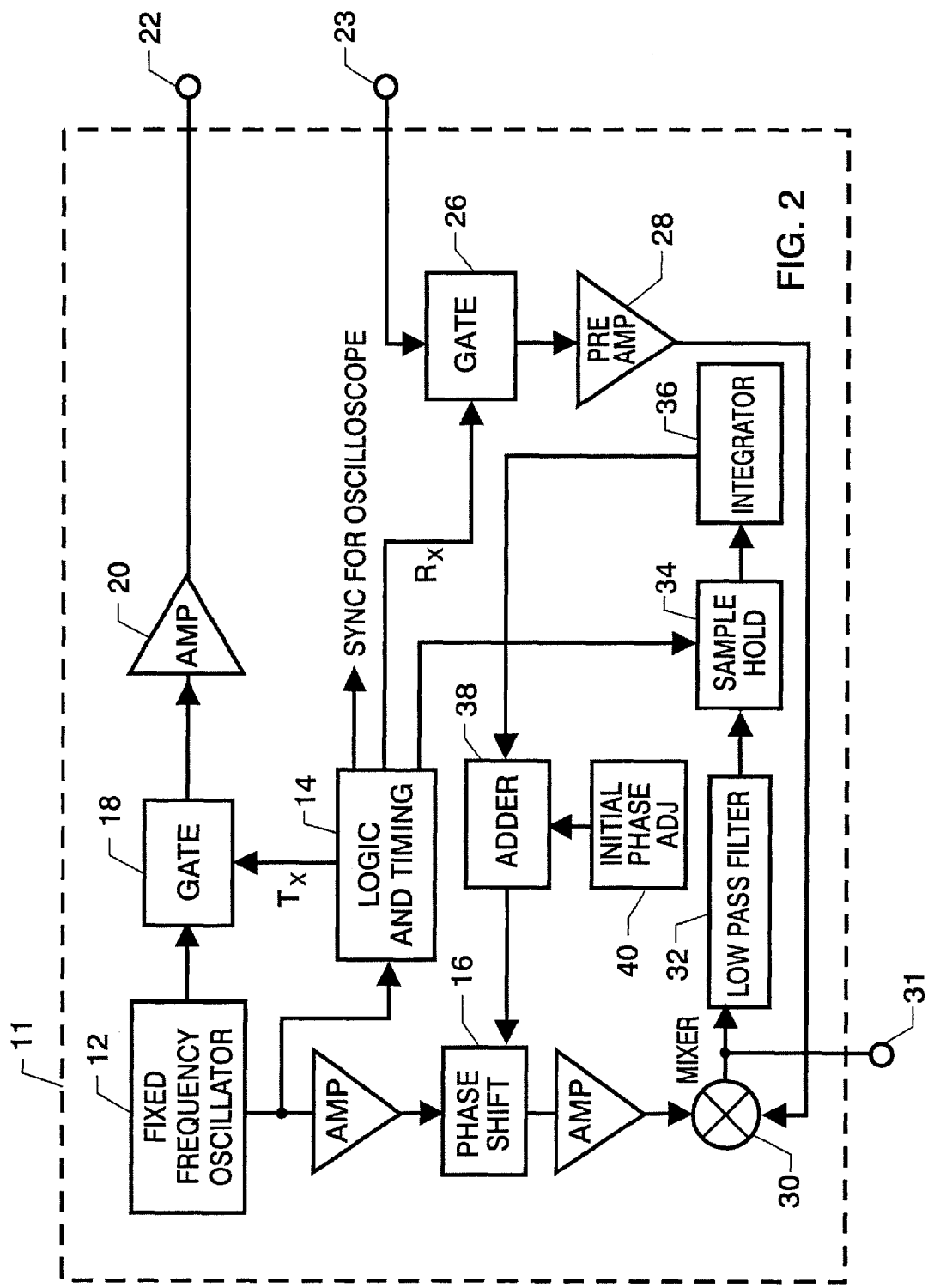
FIG. 2 is a schematic diagram of one embodiment of a measuring device that can be used in the apparatus of the present invention.

As shown in FIG. 2, the CFPPLL includes a fixed frequency oscillator 12, such as a phase-stable synthesizer. The fixed frequency oscillator 12 sends its constant frequency output to three different blocks: the logic and timing circuit 14, a buffer amplifier-phase shift circuit 16, and a tone-burst formation gate 18. The logic and timing circuit 14 uses this signal as a clock and counts down to determine the timing on its outputs. One output is the transmit or Tx gate to form the electrical tone burst. The logic and timing circuit 14 also contains a setting so that the operator can set the gate for as many cycles as is desired.

The electrical tone burst is amplified by amplifier 20 and delivered to output 22 which can be connected to a transmit transducer which is described in the ensuing description (see FIG. 1). As will be described in the ensuing description, after the electrical tone burst is received by the transmit transducer, the electrical tone burst is converted to a bulk compressional wave and is introduced to the surface of the skull which produces a surface wave. The surface wave travels a predetermined distance along the skull and is received by a receive transducer which is described in the ensuing description. The signals received by the receive transducer are inputted into input 23 of measurement device 11. A receive or Rx gate signal enables gate 26 to pass the received signal to preamplifier 28. The amplified received signal then proceeds to a mixer 30 where the amplified received signal is phase-compared to the reference signal provided from the fixed frequency oscillator 12. Unless these two signals are at quadrature, a voltage level, which constitutes an error signal, is generated by the mixer 30 and passed to output 31 and a low-pass filter 32. The output of low-pass filter 32 is inputted into a sample and hold 34, which is activated by the logic and timing circuit 14. The sample and hold 34 holds the level of voltage until the next pulse-echo cycle (P-Ec). Thus, the sample and hold output is updated at each P-Ec. This output voltage is fed to an integrator circuit 36 whose voltage output is delivered to the phase shift circuit 16 after passing through an adder circuit 38. The adder circuit 38 also receives a voltage adjustment from an initial phase adjustment 40, which may be manually operated by turning a dial. In at least one embodiment, during initial set up the operator thus changes the voltage output of the mixer 30, if necessary, by using the phase adjuster and adder circuit until the sample and hold voltage output is zero, which occurs at quadrature of the echo and the signal from the main frequency oscillator.

Thus, any change in the acoustic parameters of the surface wave propagation path defined by the skull of a patient (and the location of the transmit and receive transducers) will result in a change in the quadrature condition by an alteration in the voltage to the phase-shift circuit. One way to quantify a phase is to observe the voltage applied to the phase shifter 16. There are a variety of ways in which to quantify the phase shift. In order to measure changes in velocity, the results must be measured in terms of the phase shift caused by changes in the traversal time of the acoustical signal as the acoustic signal travels along the propagation path defined by the skull. This is affected by change in phase in either the electrical or acoustical parameters. One can use this fact to calibrate by either calibrating the phase shift circuit against input voltage and reading the input voltage changes, or inserting a known, adjustable phase shifter, such as a calibrated line stretcher (not shown, but described in U.S. Pat. No. 5,214,955, the disclosure of which patent is herein incorporated by reference) and adjusting until the same input voltage to the phase shifter is obtained.

In at least one alternate embodiment, measurement device 11 is configured as the electronic apparatus described in commonly owned U.S. Pat. No. 5,617,873, the disclosure of which is herein incorporated by reference, and indicated by numeral 30 therein.

Referring to FIG. 1 herein, apparatus 10 further includes mounting strut 50. Mounting strut 50 comprises center section 52 and movable end portions 54 and 56. End portions 54 and 56 are pivotally connected to center section 52 by pivot pins 58. Mounting strut 50 further includes transmit and receive angle blocks 60 and 62, respectively, that are attached to end portions 54 and 56, respectively. Transmit and receive angle blocks 60 and 62 have surfaces 64 and 66, respectively, that are configured for contact with a patient's head. In one embodiment, mounting strut 50 is configured to have a predetermined degree of elasticity so as to provide firm contact between surfaces 64, 66, and the head of a patient. In one embodiment, mounting strut 50 is configured so that end portions 54 and 56 are urged inward towards the patient's head so as to facilitate firm contact between surfaces 64, 66, and the head of a patient.

In another embodiment, mounting strut 50 is configured so that center section 52 is comprised of two portions that are slidably engaged with each other so that the overall length of center section 50 can be adjusted so as to accommodate skulls of varying sizes. Such a feature can be used to vary the length of the propagation path over the patient's skull thus enabling the surface wave to be launched over a relatively small propagation path, for example, the patient's forehead or any other appropriate segment of the patient's skull.

Referring to FIG. 1, apparatus 10 further comprises transmit and receive transducers 70 and 72 that are attached to transmit and receive angle blocks 60 and 62, respectively. Transmit transducer 70 is electrically connected to output 22 of measuring device 11, for example, by wire or cable 74. Similarly, receive transducer 72 is electrically connected to input 23 of measuring device 11, for example, by wire or cable 76.

Apparatus 10 can further include processing device 80 that receives the signals outputted at output 31 of measuring device 11. Processing device 80 can implement measurement interpretive algorithms in order to generate a biological time constant which is used in the analysis of the data extracted from the signal outputted at output 31 of measuring device 11. In one embodiment, processing device 80 includes electronic components and circuitry such as microprocessors, timing circuitry, data storage devices (e.g. RAM, ROM, cache, etc.), filter circuits, and other processing circuits for effecting implementation of the aforementioned measurement interpretive algorithms. In another embodiment, processor device 80 is configured as a computer that implements a computer program that effects generation of the aforesaid biological time constant.

Operation

Referring to FIG. 1, one possible mode of operation is as follows. Measurement device 11 outputs an electrical tone burst through output 22 which is carried by wire 74 and is inputted into transmit transducer 70. Transducer 70 converts the electrical tone burst into an ultrasonic bulk compressional wave. The ultrasonic bulk compressional wave passes through the transmit angle block 60 and is directed to the interface between surface 64 and the skin of the patient's skull. The ultrasonic bulk compressional wave passes into the subcutaneous tissue of the patient's skull at a predetermined angle, thereby producing a surface wave which travels along the skull. The surface wave traverses the skull along a propagation path and passes through the interface between the skin of the patient's skull and surface 66 of receive angle block 62. The receive angle block 62 receives the surface wave and passes the surface wave to the receive transducer 72. The angle at which the surface wave is received by the receive angle block is substantially the same as the predetermined angle described in the foregoing description. The receive angle block converts the surface wave into a bulk compressional wave. The receive transducer 72 converts the bulk compressional wave into an electrical waveform (i.e. an electrical tone burst). The electrical waveform is carried by wire or cable 76 to input 23 of measurement device 11.

As the patient's skull responds to ICP, the velocity of the surface wave changes thereby causing retardation or advancement of the phase of the received surface wave. Measuring device 11 measures the phase of the electrical waveform outputted by receive transducer 72 with respect to a reference signal in order to determine the change in phase between the two signals. Measuring device 11 outputs a signal at output 31 which contains data that indicates phase difference. The signal outputted at output 31 is inputted into processing device 80 which implements the measurement interpretive algorithms that determine the changes in circumferential expansion, or contraction, of the patient's skull due to changes in ICP. This circumferential expansion or contraction, for example, can be calculated either in the form of total skull circumference change or in reference to changes in a specific circumferential arc portion of the skull. These determined circumferential changes can then be utilized to determine changes in ICP.

The principles, embodiments, and modes of operation of the present invention have been described in the foregoing specification. The invention which is intended to be protected herein should not, however, be construed as limited to the particular forms disclosed, as these are to be regarded as illustrative rather than restrictive. Variations or changes may be made by those skilled in the art without departing from the spirit of the invention. Accordingly, the foregoing detailed description should be considered exemplary in nature and not limited to the scope and spirit of the invention as set forth in the attached claims.

Thus, having described the invention, what is claimed is:

1. A method for determining changes in intracranial pressure within a patient's skull comprising:

transmitting a sound wave onto the surface of the skull so as to produce a surface wave;

receiving the surface wave at a location that is a predetermined distance from where the sound wave was transmitted upon the skull;

determining the change in phase of the received surface wave with respect to a reference phase; and processing the determined change in phase to determine a change in intracranial pressure.

2. The method according to claim 1 wherein the step of processing the determined changes comprises the step of determining a change in the circumference, or a circumferential arc, of the skull.

3. The method according to claim 1 wherein:

the step of transmitting a sound wave comprises transmitting the sound wave at a predetermined angle with respect to the skull; and the step of receiving the surface wave comprises receiving the surface wave at an angle with respect to the skull which is substantially the same as the predetermined angle.

4. The method according to claim 1 wherein the step of transmitting a sound wave onto the surface of the skull comprises transmitting an ultrasonic bulk compressional wave onto the surface of the skull so as to produce the surface wave.

5. The method according to claim 1 further comprising the step of generating an electrical tone burst, and wherein the transmitting step further comprises the step of converting the electrical tone burst into the sound wave.

6. The method according to claim 1 wherein the receiving step comprises the step of converting the received surface wave into an electrical waveform.

7. The method according to claim 5 wherein the step of determining the change in phase of the received surface wave comprises the step of determining the change in phase of the electrical waveform with respect to a reference phase.

8. The method according to claim 1 further comprising the step of providing a measurement interpretation algorithm and wherein the processing step comprises the step of processing the determined change in phase using measurement interpretation algorithms to determine changes in circumferential expansion or contraction due to changes in intracranial pressure.

9. The method according to claim 1 wherein the steps of transmitting and receiving are performed at more than one location on the patient's skull.

10. An apparatus for determining changes in intracranial pressure in a patient's skull, comprising:
  a transmitting device for generating a sound wave on the surface of the skull;
  a receiving device for receiving the surface wave at a location that is a predetermined distance from where the sound wave was generated upon the skull;
  a measuring device for determining the change in phase of the received surface wave with respect to a reference phase; and
  a processing device for using the determined phase change to determine a change in intracranial pressure.

11. The apparatus according to claim 9 wherein the processing device is configured to determine circumferential expansion or contraction of the skull, wherein the circumferential expansion or contraction of the skull is determined as at least one of:
  a) a total circumference change, or
  b) a circumferential arc change.

12. The apparatus according to claim 10 wherein:
  the transmitting device is configured and disposed for transmitting the sound wave at a predetermined angle with respect to the skull so as to generate the surface wave; and
  the receiving device is configured and disposed for receiving the surface wave at an angle with respect to the skull which is substantially the same as the predetermined angle.

13. The apparatus according to claim 10 wherein the transmitting device is for transmitting an ultrasonic bulk compressional wave onto the surface of the skull at the predetermined angle with respect to the skull so as to generate the surface wave.

14. The apparatus according to claim 10 wherein the measuring device is configured to include circuitry for generating an electrical tone burst for input into the transmitting device.

15. The apparatus according to claim 14 wherein the transmitting device comprises a transducer having an input for receiving the electrical tone burst and converting it into an ultrasonic bulk compressional wave.

16. The apparatus according to claim 15 wherein the transmitting device further includes a transmit angle block having a surface that contacts the skull, the transducer being mounted to the transmit angle block.

17. The apparatus according to claim 10 wherein the receiving device comprises a receive transducer having an input for receiving the surface wave and converting the surface wave into an electrical waveform.

18. The apparatus according to claim 17 wherein the receiving device further includes a receive angle block having a surface that contacts the skull, the receive transducer being mounted to the receive angle block.

19. The apparatus according to claim 17 wherein the measuring device is configured to compare the phase of the electrical waveform to the reference phase to determine the phase difference.

20. The apparatus according to claim 10 wherein the processing device include means for implementing measurement interpretative algorithms for using the determined phase change to determine circumferential expansion resulting from a change in intracranial pressure.

21. The apparatus according to claim 10 further comprising a mounting strut, the transmitting and receiving devices being movably attached to the mounting strut.

22. An apparatus for determining changes in intracranial pressure, comprising:
  means for transmitting a wave onto the surface of the skull so as to produce a surface wave;
  means for receiving the surface wave a distance from where the wave was transmitted upon the skull;
  means for determining the change in phase of the received surface wave with respect to a reference phase; and
  means for processing the determined phase change to determine a change in intracranial pressure.

23. The apparatus according to claim 22 wherein the processing means comprises means for determining the circumferential expansion or contraction of the skull, wherein the circumferential expansion or contraction is determined as at least one of:
  a) a total circumference change, or
  b) a circumferential arc change.

24. The apparatus according to claim 22 wherein:
  the transmitting device is configured and disposed for transmitting the wave at a predetermined angle with respect to the skull so as to produce the surface wave; and
  the receiving device is configured and disposed for receiving the surface wave at an angle with respect to the skull which is substantially the same as the predetermined angle.

25. The apparatus according to claim 22 wherein the means for transmitting a wave onto the surface of the skull comprises means for transmitting an ultrasonic bulk compressional wave onto the surface of the skull.

26. The apparatus according to claim 22 wherein the means for transmitting a wave onto the surface of the skull comprises means for transmitting at least two waves onto the surface of the skull to thereby produce at least two surface waves.

27. The apparatus according to claim 26 wherein the means for transmitting at least two waves onto the surface of the skull comprises at least two transmit transducers.

28. The apparatus according to claim 22 wherein the means for receiving the surface wave comprises means for receiving at least two surface waves.

29. The apparatus according to claim 28 wherein the means for receiving at least two surface waves comprises at least two receive transducers.

30. An apparatus for determining changes in intracranial pressure in a patient's skull, comprising:
  a transmitting device for generating a wave on the surface of the skull;

a receiving device for receiving the surface wave;

a measuring device for determining the change in phase of the received surface wave with respect to a reference phase; and a processing device to utilize the determined phase change to determine a change in intracranial pressure.

31. The apparatus according to claim 30 wherein the processing device is configured to determine the circumferential expansion or contraction of the skull, wherein the circumferential expansion or contraction is determined as at least one of:

a) a total circumference change, or b) a circumferential arc change.

* * * * *